United States Patent [19]
Moore

[11] Patent Number: 5,945,578
[45] Date of Patent: Aug. 31, 1999

[54] HIGH OLEIC ACID PEANUT

[75] Inventor: Kim M. Moore, Ashburn, Ga.

[73] Assignee: Gold Kist, Inc., Atlanta, Ga.

[21] Appl. No.: 08/948,514

[22] Filed: Oct. 10, 1997

Related U.S. Application Data

[60] Provisional application No. 60/027,914, Oct. 11, 1996, and provisional application No. 60/029,063, Oct. 22, 1996.

[51] Int. Cl.$^6$ .............................. A01H 5/00; A01H 5/10; A01H 1/04; A01H 1/06; C12P 7/64
[52] U.S. Cl. ........................... 800/264; 800/270; 800/298
[58] Field of Search ........................ 435/172.1; 800/200, 800/230, 250, 255, DIG. 23, 69, 264, 270, 298; 47/58

[56] References Cited

U.S. PATENT DOCUMENTS

| | | | |
|---|---|---|---|
| 4,627,192 | 12/1986 | Fick | 47/58 |
| 4,948,811 | 8/1990 | Spinner et al. | 514/560 |

FOREIGN PATENT DOCUMENTS

| | | |
|---|---|---|
| 2 617 675 | 1/1989 | France . |

OTHER PUBLICATIONS

Sharma et al., "Fatty Acid And Amino Acid Composition Of Groundnut Mutants" *Qual Plant Plant Foods Hum Nutt*, vol. 35:3–8, (1985).

Moore et al., "The Inheritance Of High Oleic Acid In Peanut", *The Journal of Heredity*, vol. 80(3):252–253, (1989).

Knauft et al., "Further Studies On The Inheritance Of Fatty Acid Composition In Peanut", *Peanut Science*, vol. 20:74–76, (1993).

Isleib et al., "Fatty Acid Genotypes of Five Virginia–Type Peanut Cultivars", *Published in Crop. Sci.*, vol. 36:556–558, (1996).

Knauft et al., "Improved Oil Chemistry" Runner Type, Circular S 398, Dec. 1995.

Norden et al., "Breeding Of The Cultivated Peanut", *Peanut Science*, pp. 95–122 (1982).

Patel et al, eds., Am. Peanut Res. Educ. Soc. :Yoakum, Tx.

Ashri, "A Dominant Mutation With Variable Penetrance And Expressivity Induced By Diethyl, Sulfate In Peanut", *Mutation Research*, vol. 9:473–480, (1970).

Walbot, "Strategies For Mutagenesis And Gene Cloning Using Transposon Tagging And T–DNA Insertional Mutagenesis", *Annu. Rev. Plant Physiol. Plant Mol. Biol.*, vol. 43:49–82, (1992).

Konez et al., "T–DNA Insertional Mutagenesis In Arabidopsis", *Plant Molecular Biology*, vol. 20:963–976, (1992).

Ozias–Akins et al., "Regeneration Of Transgenic Peanut Plants From Stably Transformed Embryogenic Cellus", *Plant Science*, vol. 93:185–194, (1993).

McWatters et al., "Potential Food Uses Of Peanut Seed Proteins", *Peanut Science And Technology*, pp. 689–736.

Knauf, "The Application Of Genetic Engineering To Oilseed Crops", *TIBTECH*, vol. 5:40–47,(1987).

Norden, "Breeding of The Cultivated Peanut", pp. 175–208.

Baker et al., "Transposition of The Maize Controlling Element "Activator" In Tobacco", *Proc. Natl. Acad. Sci. USA*, vol. 83:4844–4848, (1986).

Yoder et al., "Ac Transposition In Transgenic Tomato Plants", *Mol. Gen. Genet.*, vol 213:291–296, (1988).

Belzile et al., "Sexual Transmission of Transposed Activator Elements In Transgenic Tomatoes", *Genetics*, vol. 123:181–189, (1989).

Lassner et al., "Genetic Transactivation Of Dissociation Elements In Transgenic Tomato Plants", *Mol. Gen. Genet.*, vol. 218:25–32,(1989).

Battey et al., "Genetic Engineering For Plant Oils: Potential and Limitations", *TIBTECH*, vol. 7:122–126, (1989).

Fedoroff, "Maize Transposable Elements", pp. 375–411.

*Primary Examiner*—David T. Fox
*Attorney, Agent, or Firm*—Foley & Lardner

[57] ABSTRACT

An Arachis hypogaea L. peanut seed, peanut plant, peanut line, peanut seed product and peanut oil having an oleic acid content of from about 80% to about 85% and a linoleic acid content of from about 1.5% to about 2.5%, each based upon the total fatty acid content of said seed and a ratio of the amount of oleic acid to linoleic acid in said seed from about 20:1 to about 58:1. The peanut seed, seed product, plant and line is of the genetic runner-type variety and has a low pod-splitting trait. 'M2-225' seeds were deposited under the Budapest Treaty on Oct. 11, 1996, at the American Type Culture Collection, 12301 Parklawn Drive, Rockville, Md. 20852 USA, Accession number 97762.

25 Claims, No Drawings

HIGH OLEIC ACID PEANUT

This is a continuation-in-part of provisional U.S. Application Serial No. 60/027,914, filed Oct. 11, 1996, and provisional U.S. Application Serial No. 60/029,063, filed Oct. 22, 1996.

FIELD OF INVENTION

The present invention is directed to a high oleic acid peanut plant line and products derived therefrom.

BACKGROUND OF THE INVENTION

Peanuts (*Arachis hypogaea* L.) are grown worldwide in the tropic and temperate zones for seed oil and human foods such as peanut butter, roasted seed and confections. The final quality of edible peanuts is due principally to the chemical composition of the oil, protein and carbohydrate fractions of the seed. Since fatty acids make up the major portion of the weight of an oil molecule, the physical and chemical properties of the oil tend to be determined by the properties of the fatty acids which predominate in their makeup. Oils high in monounsaturates are desirable for both improved shelf life and potential health benefits.

Depending upon the intended oil use, different fatty acid compositions are desired. Peanut breeders face the dilemma of satisfying both the requirement of the manufacturer, which is stability of the processed product, and the demand from consumers for an increased polyunsaturated to saturated (P/S) ratio.

Oil stability and nutritional quality are both dependent on the relative proportions of the saturated and unsaturated fatty acids that constitute the oil. Moore, K. M. et al., *J. Heredity* 80 (3):252 (1989). Oxidative rancidity increases with increased levels of polyunsaturated fatty acids. Oxidation of the carbon double bonds of fatty acids produces acids, aldehydes, ketones, and other hydrocarbons that cause odors and flavors commonly associated with rancidity. St. Angelo, A. I. et. al., *J. Am. Peanut Res. Educ. Assoc.* 5: 128–133 (1973). The total amount of unsaturation, therefore, is inversely proportional to the keeping quality of the oil. The iodine value (IV) is a measure of oil chemical stability, with oils having higher IV being more unsaturated and chemically less stable. Low linoleic acid content ensures a product of high storage stability. Norden, A. J., WPI Accession No. 89-070645/10.

The American Heart Association and the American Health Foundation have recommended diet modifications to achieve lower serum cholesterol levels in the population. These diet modifications include reducing consumption of saturated fatty acids and thereby increasing the polyunsaturated to saturated (P/S) ratio in the diet. Technical Committee, *Food Fats and Oils,* 5th ed. (1982). Edible peanut oils with a higher percentage of unsaturated fatty acids are desired for these cardio-vascular health reasons. Mattson, F. H. et al., *J. Lipid Research* 26: 194–202 (1985).

High levels of the long-chain saturated fatty acids, arachidic and behenic are undesirable as they were suggested as being the responsible toxic element for enhancing atherosclerosis in rabbits fed diets utilizing peanut oil. Diets high in monounsaturates are able to lower serum cholesterol in a fashion similar to diets low in low fat. Grundy, S. M., *New England J. Medicine* 314(12): 745 (1986); Nutrition Foundation, Inc., *Nutrition Review* 30(3): 70–72 (1973). High levels of the monounsaturated oleic acid, which is present in olive oil, is as effective as the polyunsaturated linoleic acid in lowering the blood plasma cholesterol. Mattson, F. H., et al., *J. Lipid Research* 26: 194–202 (1985).

Although as many as 12 fatty acids have been reported in peanuts, only three are present in amounts exceeding 5%: palmitic, oleic and linoleic. Ahmed, E. M. et al. in *Peanut Science and Technology* (1982 H. E. Pattec, et al., ed.). These three fatty acids comprise about 90% of the fatty acid composition of the oil, with oleic and linoleic comprising about 80%. The remainder of the fatty acids comprise about 10%, each ranging in concentration from 0.02% to 2.59%.

Several factors affect the fatty acid composition of peanut oil: maturity, temperature, planting date, location, market grade, and peanut genotype. Moore, et al., supra; Cobb, W. Y. et al. in *Peanuts-Culture and Uses* (1973). Since 1970, studies on the genetic variability in the fatty acid composition of peanut genotypes have shown a range in the composition of the different acids. Norden, A. J., et al. *Peanut Science* 14:7–12 (1987).

Peanut genotypes are known with as low as 21% oleic and as high as 43% linoleic acid. One investigator sub-divided 100 peanut genotypes into three maturity groups and into four U.S. market-types. Bovi, M. L. A. Ph.D. Dissertation, University of Florida (1982). A large variation in oil quality was found within each market-type and/or maturity group. A peanut line with 79.91% oleic acid and 2% linoleic acid has been reported. Norden, et al., supra.

Fatty acid composition has been determined among seven U.S. runner-type peanut cultivars: 'Florunner', 'Sunrunner', 'GK-7', 'Southern Runner', 'Sunbelt Runner', and 'Okrun'. Branch, W. D. et al., *J. Am. Oil Chem. Soc.* 67(9: 591–593 (1990). Variety 'GK-7' is described in Plant Variety Protection certificate 82001413. Significant year and cultivar differences are found within these fatty acid profiles. Southern Runner had the greatest oleic to linoleic ratio of 2.3 and iodine values of 90.5. 'Florunner' and 'Sunrunner' were the highest in unsaturated and lowest in saturated and long-chain fatty acids. 'Florunner' exhibits 51.7% oleic acid and 29.8% linoleic acid, while 'GK-7' exhibits 49.6% oleic acid and 30.5% linoleic acid. 'GK-7' and 'Florunner' are the most widely cultivated peanut varieties in the United States.

Major genes for fatty acid composition have been reported in three oilseed crop species: sunflower (*Helianthus annuus* L.), soybean (*Glycine max* L. Merr.), and rapeseed (*Brassica napis* L.) Urie, A. L., *Crop Sci.* 25:986–989 (1985); Brunklaus-Jung E. et al., *Plant Breeding* 98:9–16 (1987); Erickson, E. A., et al., *Crop Sci.* 28: 644–646 (1988); Rennie, B. D. et al., *Crop Sci.* 28: 655–657 (1988).

Artificial irradiation has been used to induce changes in peanut lines to produce Spanish improved groundnut mutants that produce high oleic acid and low linoleic levels. More specifically, a parental Spanish improved line with 39% oleic acid was irradiated to make mutants that produce 61% oleic acid. Sharma, N. D., et al., *Qual. Plant Foods Hum. Nutr.* 35: 3–8 (1985).

The variation in oil quality among diverse peanut genotypes has been determined. Norden et al., supra. The range in the percent of the saturated fatty acids found among peanut genotypes in the Florida breeding program is not widely different from the ranges reported in other lines. Id. Oleic acid (18:1) levels in the oil of cultivated peanut (*Arachis hypogaea* L.) have been reported as 36% to 81.4% of the total fatty acid composition. Moore, K. M., et al., *J. Heredity* 30(3) :252–253 (1989); Knauft, D. A., et al., *Peanut Science* 20: 74–76 (1993) and Norden, et al., supra. A Spanish type high-oleic-acid peanut line, designated F435, exhibits 79.91% oleic acid and 2% linoleic acid. Moore, K. M. et al., supra. The peanut line F435 produces peanut seeds with an oleic acid content about 74–79.91% and linoleic acid content about 2–8%, based on total fatty acids, and an oleic acid:linoleic acid ratio of 9–42:1. French Patent Application 2617675 (See Tableau 1).

Initial genetic studies of the F435 peanut line showed that a single recessive gene controlled its fatty acid composition trait in two genetic backgrounds and a second recessive gene was necessary for expression in a third background. Moore, K. M. et al., supra. Further studies have shown that the high-oleic-acid trait in F435 is of monogenic inheritance in 12 parental backgrounds and digenic inheritance in one background. Knauft, D. A., et al., *Peanut Sci.* 20(2):74–76 (1993). This suggested that either one of the two recessive genes may be common in the Spanish variety peanut germplasm, and that crosses could be expected to segregate in simple monogenic ratios. Knauft, et al., supra. More recently, the number of genes controlling inheritance of the high oleic acid trait in F435 has been determined. Isleib, T. G., et al., *Crop Science* 36(3): 556–558 (1996). Segregation ratios of populations derived from crosses with NC-7, NC-9, NC-10C, and VA-C92R were consistent with a monogenic model and inconsistent with the digenic model. The activity of delta-12-desaturase, which catalyzes the conversion of oleate to linoleate, has also been shown to be greatly decreased in the F435 line. Ray, T. K. et al., *Plant Sci.* 91(1):15–21 (1993).

When the proportion of genes from F435 is reduced through backcrossing to less than 0.8%, fatty acid composition remains similar to the original F435 line. However, the concentration of oleic acid in F435 has never been shown to be greater than 79.91%. French Patent Application 2617675 (See Tableau 1); Brazil Patent Application 8803439; Japan Patent Application 1091720 and China Patent Application 1030691. One backcross made between F435 and F519.9, with F519.9 as the recurrent parent, resulted in a backcross having an oleic acid composition of 81.4=/−0.4%. Knauft, D. A., et al., *Peanut Sci.* 20(2):74–76 (1993). Also, the concentration of linoleic acid in F435 has never been shown to be less than 2.14%. French Patent Application 2617675 (See Tableau 1).

The high oleic acid trait of F435 has been transferred from the Spanish-type variety to one variety of runner-type to produce the commercially available runner-type peanut variety 'SunOleic® 95R'. University of Florida Circular S 398 'SunOleic® 95R'. 'SunOleic® 95R' does not yield as well as other runner-type varieties and exhibits appreciable pre-harvest pod-splitting. Id.

A need, therefore, remains for alternative sources of a high oleic acid characteristic that can be introgressed into diverse peanut backgrounds. In addition, a need exists for a high oleic acid characteristic peanut of the runner-type variety that has the additional characteristics of acceptable or high yield and negligible pod-splitting.

SUMMARY OF THE INVENTION

Embodiments of the present invention, therefore, provide a new peanut plant line of the runner-type variety that produces peanut seeds having a high oleic acid content that is at least 80% of the total fatty acids and a low linoleic acid content that is less than 2% of the total fatty acids. A further embodiment of the present invention provides a new peanut plant line that produces peanut seeds having a high oleic acid content greater than 80% and a low linoleic acid content less than 2%, in combination little or with no pod splitting. A further embodiment of the present invention provides a new peanut plant line that produces peanut seeds having a high oleic acid content greater than 80% and a low linoleic acid content less than 2%, in combination with acceptable or high yield. Yet a further embodiment of the present invention provides a new peanut plant line that produces peanut seeds having a high oleic acid content greater than 80% and a low linoleic acid content less than 2%, in combination with little or no pod splitting and acceptable or high yield.

Another embodiment of the present invention provides a new peanut plant line that produces peanut seeds having a high oleic acid content greater than 80% and a low linoleic acid content less than 2%, in combination with little or no pod splitting, acceptable or high yield and acceptable milling characteristics. Acceptable milling characteristics include a grade of 75 and acceptable blanching. A grade of 75 means that 75% of the weight of the unshelled peanuts are comprised of nutmeats and seed coat while 25% of the weight is comprised of hulls and damaged kernels. Acceptable blanching means that the seed coat is removed easily without splitting the seeds in half.

Yet another embodiment of the present invention provides a new peanut seed having an oleic acid content of from about 80% to about 85% and a linoleic acid content of from about 1.5% to about 2.5%, each based upon the total fatty acid content of the seed and a ratio of the amount of oleic acid to linoleic acid in the seed from about 7:1 to about 80:1, in combination with little or no pod splitting, acceptable or high yield and acceptable milling characteristics.

Yet a further embodiment of the present invention provides a new peanut seed having an oleic acid content of from about 80% to about 85% and a linoleic acid content of from about 1.5% to about 2.5%, each based upon the total fatty acid content of the seed and a ratio of the amount of oleic acid to linoleic acid in the seed from about 7:1 to about 80:1, where the seed is the product of a peanut plant having the characteristics of a line designated 'M2-225'.

Yet another aspect of the present invention is to provide a new peanut seed having an oleic acid content of from about 80% to about 85% and a linoleic acid content of from about 1.5% to about 2.5%, each based upon the total fatty acid content of the seed and a ratio of the amount of oleic acid to linoleic acid in the seed from about 7:1 to about 80:1, where the seed is the product of a peanut plant of the runner-type genetic background. Another embodiment of this invention is a seed that it is a product of a peanut plant having the characteristic of low pod splitting.

A further embodiment of the present invention provides a peanut plant which produces seeds having an oleic acid content from about 80% to about 85% and a linoleic acid content of from about 1.5% to about 2.5%, each based upon a total fatty acid content of the seed and a ratio of the amount of oleic acid to linoleic acid in the seed from about 7:1 to about 80:1, in combination with little or no pod splitting, acceptable or high yield and acceptable milling characteristics.

Yet another embodiment of the present invention provides a peanut plant which produces seeds having an oleic acid content from about 80% to about 85% and a linoleic acid content of from about 1.5% to about 2.5%, each based upon a total fatty acid content of the seed and a ratio of the amount of oleic acid to linoleic acid in the seed from about 7:1 to about 80:1 where the plant has the characteristics of a line designated 'M2-225'. A further embodiment of the present invention provides such a plant that is of the runner-type genetic background and/or has the characteristic of low pod splitting.

A further embodiment of the present invention provides a *Arachis hypogaea L.* seed product consisting essentially of a substantially homogenous assemblage of peanut seeds having an oleic acid content of from about 80% to about 85% and a linoleic acid content of from about 1.5% to about 2.5%, each based upon the total fatty acid content of the seed and a ratio of the amount of oleic acid to linoleic acid in the seed from about 7:1 to about 80:1.

An embodiment of the present invention provides such a seed product having an oleic acid content that is about 80–85%. A further embodiment of the present invention provides such a seed product having a linoleic acid content that is about 1.5–2.5%. Another embodiment of the present invention provides an *Arachis hypogaea* L. seed product consisting essentially of a substantially homogenous assemblage of peanut seeds having an oleic acid content of from about 80% to about 85% and a linoleic acid content of from about 1.5% to about 2.5%, each based upon the total fatty acid content of the seed and a ratio of the amount of oleic acid to linoleic acid in the seed from about 7:1 to about 80:1 in which the seed product is from a peanut plant having the characteristics of a line designated 'M2-225'.

Yet another embodiment of the present invention provides such a seed product in which the seed is the product of a peanut plant that is of the runner-type genetic background. A further embodiment of the present invention provides a seed product that has an oleic acid content that is about 80–85%. A further embodiment of the present invention provides such a seed product having a linoleic acid content that is about 1.5–2.5%. Another embodiment of the present invention provides such a seed product that is made form peanut seed that is the product of a peanut plant that has the characteristic of low pod splitting.

Another embodiment of the present invention provides a peanut line consisting essentially of a substantially uniform population of *Arachis hypogaea* L. plants which produce seed having an oleic acid content of from about 80% to about 85% and a linoleic acid content of from about 1.5% to about 2.5%, each based upon the total fatty acid content of the seed and a ratio of the amount of oleic acid to linoleic acid in the seed from about 7:1 to about 80:1. A further embodiment of the present invention provides such a peanut line where the oleic acid content is about 80–85%. Yet another embodiment of the present invention provides such a peanut line in which the linoleic acid content is about 1.5–2.5%.

Another embodiment of the present invention provides a peanut line consisting essentially of a substantially uniform population of *Arachis hypogaea* L. plants which produce seed having an oleic acid content of from about 80% to about 85% and a linoleic acid content of from about 1.5% to about 2.5%, each based upon the total fatty acid content of the seed and a ratio of the amount of oleic acid to linoleic acid in the seed from about 7:1 to about 80:1 in which the plants of the peanut line have the characteristics of a line designated 'M2-225'.

Yet a further embodiment of the present invention provides a peanut line where the plants are of the runner-type genetic background. Another embodiment of the present invention provides a peanut line in which the plants have the characteristic of low pod splitting.

Yet another embodiment of the present invention provides peanut oil derived from a seed having an oleic acid content of from about 80% to about 85% and a linoleic acid content of from about 1.5% to about 2.5%, each based upon the total fatty acid content of the seed and a ratio of the amount of oleic acid to linoleic acid in the seed from about 7:1 to about 80:1. A further embodiment of the present invention comprises a peanut oil in having an oleic acid content about 80–85%. A further embodiment provides a peanut oil in which the linoleic acid content is about 1.5–2.5%. Yet another embodiment of the present invention is a peanut oil derived from a seed having an oleic acid content of from about 80% to about 85% and a linoleic acid content of from about 1.5% to about 2.5%, each based upon the total fatty acid content of the seed and a ratio of the amount of oleic acid to linoleic acid in the seed from about 7:1 to about 80:1 in which the seed is the product of a peanut plant having the characteristics of a line designated 'M2-225'.

A further embodiment of the present invention provides a peanut oil in which the seed is the product of a peanut plant that is of the runner-type genetic background. Another embodiment of the present invention provides peanut oil derived from seed that is the product of a peanut plant that has the characteristic of low pod splitting.

Yet another embodiment of the present invention provides a peanut seed in which the ratio of the amount of oleic acid to linoleic acid in the seed is from about 20:1 to about 58:1. A further embodiment of the present invention provides peanut seed where the seed is the product of a peanut plant having an acceptable milling characteristic. A further embodiment of the present invention provides a peanut seed that has acceptable milling characteristic that consist of a grade of at least about 75 and acceptable blanching.

Another embodiment of the present invention provides a peanut plant with seeds having an acceptable milling characteristic combined with the high oleic acid trait.

DETAILED DESCRIPTION OF THE PREFERRED EMBODIMENTS

1. Definitions

For the purposes of the present description, the terms "cultivar" and "variety" are used synonymously to refer to a group of plants (e.g., runner-type within a species (*Arachis hypogaea* L.) which share certain constant characters that separate them from the typical form and from other possible varieties within that species. While possessing at least one distinctive trait, a variety like 'M2-225' is also characterized by a uniformity among individuals within the variety, based primarily on the Mendelian segregation of traits among the progeny of succeeding generations.

A "line," as distinguished from a "variety," denotes a group of plants which display less variation between individuals, generally (although not exclusively) by virtue of several generations of self-pollination. In addition, a "line" is defined, for the purpose of the present invention, sufficiently broadly to include a group of plants vegetatively propagated from a single parent plant, using culture techniques.

A variety or a line is considered "true-breeding" for a particular trait if it is genetically homozygous for that trait to the extent that when the true-breeding variety or line is self-pollinated, a significant amount of independent segregation of the trait among the progeny is not observed.

The content of various fatty acids, such as oleic and linoleic, which is characteristic of oil from a given seed sample is commonly expressed as a percentage of the total fatty acid fraction in the oil. This convention will be followed for the following description, unless otherwise indicated. The ratios of oleic acid content to linoleic acid content are calculated by dividing the linoleic acid percentage of total fatty acids by the like percentage of oleic acid.

The novel peanut of the present invention reproducibly expressed the high oleic acid trait of the runner-type cultivar against a phenotypic background of acceptable seed yield, and low pod-splitting, and other agronomic characteristics which are sufficiently consistent for commercial applications. In contrast, the original cultivar did not display the high oleic trait.

Embodiments of the invention provide seeds having an oleic acid content of at least about 80% (e.g., at least 80%, including, e.g., 80%, 81%, 82%, 83%, 84% and 85%), at least about 81% (e.g., at least 81%), at least about 82% (e.g., at least 82%), at least about 83% (e.g., at least 83%), at least about 84% (e.g., at least 84%), and at least about 85% (e.g., at least 85%).

The pod splitting characteristics of embodiments of the invention can be compared with any other peanut variety using yield trials, both within a particular location and between locations. The trials can be arranged in a Randomized Complete Block design with replications. Each plot size had 2 rows that were each 20 feet long. Yield is determined as the pounds of unhulled peanuts per acre. To measure the pod splitting characteristic, a 500 gram sample is taken from each plot and all split pods were removed and weighed. A percentage of the total plot weight was calculated for the split pod portion. When the number of split pods was less than two, the sample results were recorded as <0.10%. The term "low or negligible pod-splitting" is defined as less than 1.0% of the total plot weight being comprised of a split pod portion.

Peanuts of this invention exhibit pod-splitting in substantially less than 1.0% of the pods. Advantageous embodiments of the present invention provide pods where splitting occurs in less than about or equal to about 0.99% (e.g., less than or equal to about 0.99%), less than about 0.95% (e.g., less than 0.95%) less than about 0.9% (e.g., less than 0.9%), less than about 0.8% (e.g., less than 0.8%, less than about 0.7% (e.g., less than 0.7%), less than about 0.5% (e.g., less than 0.5%), less than about 0.4% (e.g., less than 0.4%), less than about 0.3% (e.g., less than 0.3%), and less than about 0.2% (e.g., less than 0.2%). Particularly advantageous embodiments of the present invention provide low or negligible pod-splitting. The term "low or negligible pod-splitting" is defined as less than 1.0% of the total plot weight being comprised of a split pod portion. The frequency of pod-splitting found in 'M2-225' is compared to that found in 'AT-108' and 'SunOleic® 95R' in Tables 3 and 4. The 'SunOleic® 95R' produce a total plot weight comprised of 10% or greater split pod portion.

Acceptable yield means yields that are, on a weight percent basis, at least about 70%, or preferably higher, of the yield of a commercially available variety in the same market class, when grown under average growing conditions in a replicated field trial comparison, using a randomized complete block design with four replications. Commercially available varieties in each market class include: (1) within the runner-type market class: 'AT-108', 'GK-7', 'Florunner'; (2) within the Virginia market class: 'GK-3', (3) within the Peruvian market class: 'Peruvian runner', (4) within the Valencia market class: 'Valencia', and (5) within the Spanish market class: 'Spanish', and 'F435'.

A high yield for runner type market class varieties means, on a weight percent basis, a yield that is greater than a yield obtained with 'SunOleic® 95R', when grown under average growing conditions in a replicated field trial comparison, using a randomized complete block design with four replications. Such high yields may be 5%, 10%, 15%, 20% or greater than 'SunOleic® 95R'.

'M2-225' seeds were deposited under the Budapest Treaty on Oct. 11, 1996, at the American Type Culture Collection, 12301 Parklawn Drive, Rockville, Md. 20852 USA, Accession number 97762.

2. Mutagenesis

The use of mutagenic agents to create genetic diversity in peanuts as well as useful peanut mutants has been described. Norden, A. J., et al., Breeding of the cultivated peanut in *Peanut Science and Technology,* the entirety of which is incorporated herein by reference. Peanut mutants may be induced by γ-irradiation according to the method of Sharma, et al. *Qual. Plant Foods Hum. Nutr.* 35:3–8 (1985), the entirety of which is incorporated herein by reference. Methods for inducing mutations in peanut seeds chemically are also available. Ashri, A. Mutation Research, 9:473–480 (1970).

One single plant mutation experiment was conducted in North Carolina with peanuts. Starting with a uniform variety of "Virginia Bunch" peanuts, 75,000 seeds were X-rayed with doses ranging from 10,000 to 18,500 r. From these, 84,213 $M_2$ plants and about 250,000 $M_3$ plants were grown. Intensive mutation research on peanuts was continued over a period of 30 or more years.

From the progeny of the irradiated peanuts both macro- and micromutants were identified. The visible macromutants included various morphological changes in leaf size, leaf shape, branching system; induced resistance to leaf spot and potato leafhopper; and other plant characteristics. Many of the macromutations are being maintained in the peanut germ plasm collections. Along with the visible or macromutations, some of which were simply inherited, quantitative changes in the background genotypes both injurious and beneficial were also induced. This suggested that selection for the beneficial changes could lead to improvements in the genotype. Hybridization between selections from different families led in some cases to apparent yield increases, presumably due to heterosis effects of mutated genes. The peanut variety "NC4X", selected from the irradiated material because it had less pod cracking, was released and grown in commercial production for a limited period. Several genotypes have been released in which desirable mutant characteristics have been incorporated by hybridization.

The radiation experiment with peanuts is important to plant breeders because it focused attention on the small genetic changes in quantitative characteristics, such as yield or seed size, that may be induced, as well as the macromutations. Several of the induced mutations, potato leafhopper resistance for example, are being incorporated into conventional breeding programs. On the negative side, no commercial varieties of peanuts with improved yields were developed from this mutation breeding experiment.

Mutagenesis of *Arachis hypogaea L.* is usually performed by treating the seed with the mutagen, letting the surviving seeds germinate, and then recovering the progeny for analysis. The plant generation that grows from the treated seeds is referred to as the M1; it should contain heterozygote chimeras for any given mutation. Progeny collected after selfing are referred to as the M2 generation, and should be segregating both heterozygotes and homozygotes for a given mutation. The existence of heterozygotes in the M2 is particularly important if the mutation of interest turns out to be sterile or lethal when homozygous.

Treating seeds with a mutagen is not equivalent to treating a single cell. The seed after mutagenesis will be a chimeric individual, containing some nonmutant cells and a variety of cells that have mutations in their DNA. The seed will be chimeric not only for wild type versus mutant, but will also be chimeric for multiple mutations. The cells that matter are the ones that will contribute to the next generation, the M2. Mutations that are in cell lineages that do not lead to the germ line will be lost. Li and Rédei have estimated that there are two precursor cells to the germ line in the peanut seed, based on patterns of genetic segregation in the progeny of just mutagenized seeds. Studies in tobacco and maize of the shoot apex using chimeral/clonal-analysis/fate-mapping suggest that the number of cells in the seed that give rise to the upper body of the shoot and the reproductive organs is quite small, with three cells being a reasonable approximation. Poethig, R. S., Clonal analysis of cell lineage patterns in the shoot apical meristem of the germinating maize embryo, *Am. J. Bot.,* 74. 5814, (1987); McDaniel, C. N. et al., Cell lineage patterns in the shoot apical meristem of the germinating maize embryo, *Planta.* 175: 13 (1988); Poethig, R. S., A non-cell autonomous mutation regulating juvenility in maize. *Nature.* 336: 82 (1988). In other words, the goal of seed mutagenesis is to target the roughly two to three cells that will give rise to the reproductive tissues later in development. A second consequence is that a given M1 plant may have several independent mutant cell lineages. Seeds collected from pods on one portion of the M1 shoot may be genetically different from those collected at another position on the same shoot.

The variety of peanut chosen as the wild type starting material deserves some consideration. It is worth knowing the lineage of the seeds obtained; i.e., where did the investigator's source get the seeds, how many times have they been propagated, etc?

a. Mutagenize with DES

Diethyl sulphate (DES), a base alkylating agent, works well in seed mutagenesis of *Arachis hypogaea L*. Expressed in terms of killing versus mutagenesis, as described below, DES has a high induced mutation rate versus its toxicity. At optimum doses for total mutant recovery, more mutants are likely to be obtained from DES than other mutagens. However, there is considerable merit to other mutagens, in spite of the efficacy of DES. As already discussed, for proper interpretation of a mutational analysis, one would prefer to have a gene knockout/amorph. DES yields some of these, but it also gives many hypomorphs. DES induced mutations cannot be rapidly characterized at the DNA level; one usually must start with restriction fragment length polymorphisms (RFLPs) and then walk to the locus in order to clone the gene.

b. Dose of Mutagen

Usually mutagenesis is a balance between killing the treated cells versus increasing the yield of mutants with a higher dosage. After mutagenesis one needs also to have readily scorable markers to assess the induced mutant frequency. An additional consideration is the frequency with which multiple mutants can be expected to occur, and hence the probability that the phenomenally interesting phenotype just discovered is the product of twelve interacting loci, not one.

c. Killing Seeds vs. Creating Mutants

One rational way to choose a dose of a mutagen is to select the dose that will optimize the total yield of mutants. A very simple calculation suggests that the optimum mutagen dose can be calibrated initially based on the percent seed survival.

N=number of mutants
N=number of seeds, alive or dead
l=fraction of seeds alive after mutagenesis
m=fraction of seeds mutant among those alive
d=mutagen dose
k=exponential survival constant
j=linear dose response constant The number of mutant seeds after mutagenesis will be $$M=mlN$$

Assume exponentially declining survival of seeds and linearly increasing fraction of mutants with dose of mutagen:

$$l=e^{-kd} \text{ and } m=jd$$

Substitute these assumptions into the basic equation:

$$M=jde^{-kd}N$$

To optimize the total yield of mutants, take the derivative of M with respect to d, set equal to O, and then solve for d:

$$dM/dd=O \text{ and } d=1/k$$

Substituting this dose back into l gives:

$$l=e^{-k/k}=d^{-1}=0.368$$

This simple calculation thus suggests that the optimum yield of mutants, when considering both increasing seed death and increasing mutant yield as a function of mutagen dose, should occur when the mutagenized seed survival, relative to wild type, is about 37%.

d. Scoring the Increase in Mutant Frequency

The ultimate measure of success is the production of mutants. A relatively simple and quick method for doing this is the use of embryonic-lethals, as pioneered by Meinke. Embryonic-lethal mutations are, by definition, expressed very quickly after fertilization. They can be scored directly in the siliques of the M1 plants, appearing as a 3:1 segregation of pale white embryos instead of the normal green. Since many loci can yield embryonic-lethals, the frequency of this phenotype can be relatively high. After a successful DES mutagenesis, the percentage of M1 plants segregating embryonic lethals is typically 5 to 10%. Many investigators will do a quick dose response curve for each new batch of mutagen, to make sure it has the desired efficacy. It is also possible to score the frequency of albinos in the M2, or the frequency of albino chimeras in the M1, as another measure of general mutagenesis. These frequencies will be on the order of 1 in 5000 to 1 in 250 after a successful DES mutagenesis.

In the terms of the previous theoretical section, scoring mutant frequency as a function of surviving plants is a measurement of the dose-response curve, while scoring mutant frequency as a function of treated seeds measures the combination of both dose-response and seed kill.

e. Sample Protocol

An overview of mutagenesis and a sample DES mutagenesis protocol are given below. The basic strategies can be used with a variety of chemical mutagens, provided that the dose of mutagen is calibrated against seed survival and/or increase in mutant frequency.

i. Use of M1 Seed Pools: Independence and Sterile or Lethal Mutants

How does one collect the seeds from the M1 plants? One method for harvesting seeds from M1 plants is to harvest the plants and put all of the M2 seeds in one bag. Alternatively, seeds from each M1 plant are harvested individually. The seeds are then planted in soil for selection or screening. Mutagenized seeds from large seeded plants are collected on a plant by plant basis.

ii. Outline of *Arachis hypogaea L*. Seed Mutagenesis Strategy

1. Estimate needed M1 and M2 sizes based upon the desired number of mutants to isolate and the expected mutant frequency.
2. Choose mutagen based on efficacy and need for specific types of mutations, such as deletions, for further experiments. Find out how to neutralize or detoxify the mutagen if it is a chemical.
3. Do a survival curve for the mutagen, comparing survival and germination frequency after treatment at a variety of doses. Pick a dose that gives 35 to 40% survival compared to the zero dose control.
4. Choose the pool size of M1 plants. A useful number is the square root of the projected total M1 population.
5. Begin mutagenizing the seeds and plant the M1 generation. It may be convenient to plant all the M1 plants for a given pool in greenhouse flats and transplant sprouted seed to field plots.
6. Collect M1 seeds and keep separated by plant.
7. Plant sufficient M2 seeds to get a 95% representation of each M1 plant.
8. Select or screen mutants as appropriate.

9. If the phenotype of the mutant is a recessive lethal or sterile, replant the critical M1 plant seeds in an organized manner, so that heterozygotes segregating for the mutant can be identified.

iii. Mutant Characterization

1. If more than one mutant of similar phenotypes develops, choose only one mutant from each M1 plant to characterize.
2. Backcross the mutant to wild type at least five times. This process can be accelerated by crossing presumptive heterozygotes and then using progeny analysis to check the phenotype of the heterozygotes.
3. Begin mapping the mutant to chromosomes using standard visible, RFLP, selectable, or other markers.
4. Cross independent mutants from different M1 pools with each other for a complementation test to determine the number of loci identified or the number of alleles per locus.
5. Cross new mutants with other similar mutants to test for interactions between loci.
6. Determine the developmental stage at which the mutant phenotype diverges from the wild type phenotype.

f. Typical DES Mutagenesis Protocol

Use 1.5% v/v DES (diethyl sulfate). Safety Precautions: wear gloves, work in a fume hood, and neutralize DES solutions, glassware, gloves, etc. with 1M NaOH.

0. Before doing this protocol on a large scale, estimate dose versus the percent survival and germination under the given conditions and current batch of DES. Also, check for the frequency of embryonic lethals or albinos induced by each dose of the mutagen.
1. Place dry seeds in a beaker that is large relative to the volume of seeds. Add the DES solution, and incubate 20 min with occasional stirring.
2. Wash seeds with distilled water for 1 h. Change the wash every 10 to 15 min. About halfway through the washes, transfer seeds to a fresh beaker.
3. Plant seeds in soil. Thoroughly soak the soil ahead of time and then sow the seeds in an even distribution across the soil.
4. Keep careful track of the survival rate and actual number of plants in the M1 generation. Collect seeds from the M1.
5. Plant sufficient M2 seeds to obtain a 99% representation of each M1 plant. Screen or select for mutants. Keep good records of the origin of each batch of seeds, so that it can be determined whether similar mutants are independent or not.

Obviously, collecting seeds in one pool is easier. The process of collecting seeds from each individual plant and then planting individually has multiple advantages. First, if two mutants are identified with the same phenotype, one can be sure they are of independent origin; if they fail to complement each other, then two alleles have been isolated at the same locus. Second, if the phenotype entails sterility or lethality, then the mutation can be recovered from its heterozygous sibling seeds. The sectors of the M1 plant containing the mutation are heterozygous, so their selfed progeny are naturally segregating heterozygotes for the mutation as well as homozygotes. The phenotypically normal progeny from the same plant will contain some +/m heterozygotes, which can be identified in turn based on analysis of their progeny. Careful bookkeeping and collecting of seeds from each M1 plant individually thus allow one to recover sterile or lethal mutants, as well as to be absolutely sure that all mutants of the same phenotype are independent.

g. Biochemical Mutant Selection

Mutants can be identified by selection. The metabolic pathways of plants are not as well defined as those in bacteria, yeast, or mammalian systems. Sometimes plants have different pathways than the textbook paradigms; sometimes plants have alternative pathways. The metabolic diversity of plants is extraordinary. For these reasons, a mutational analysis of a plant metabolic pathway will often help define the biochemical steps in that pathway. Characterization of a biochemical mutant will usually be more complex than simply looking up the pathway and rapidly deducing the afflicted gene product. To identify oil chemistry variants, oil is extracted from $M_2$ seeds and analyzed to determine their fatty acid profile using gas chromatography. Mutants are identified based on the absence or superabundance of a particular chromatography peak. The success of this mutational analysis allowed the investigators to define the fatty acid biosynthetic pathway in Arabidopsis. Direct biochemical screening such as this can be successful if the assay is relatively quick and if a labor force exists to perform several thousand assays. Since multiple fatty acids could be monitored on one chromatogram, the screening method simultaneously searches for mutants in more than one gene, thereby increasing the probability of finding any one mutation. The delineation of fatty acid biosynthesis in Arabidopsis this way is an achievement that can serve as a useful model for peanut.

3. Breeding Selection

Methods for producing novel peanut hybrids through selection are known in the art. Each of the following references is incorporated in its entirety, herein, by reference: Moore, K. M. et al., *J. Heredity* 80(3): 252 (1989); Norden, A. J., *Peanuts, Culture and Uses*. Am. Peanut Res. and Educ. Soc., Stillwater, Okla. (C. T.Wilson ed. 1973); Norden, A. J. in *Hybridization of Crop Plants* (H. H. Hadley ed. 1980); Norden, A. J., et al., Breeding of the cultivated peanut in *Peanut Science and Technology*, (H. E. Pattee ed. 1992); Norden, A. J. et al. *Florida Agr. Res.* 3:16–18 (1984).

Single plants are selected through early generations of a cross. Different plants are combined only when they approach genetic uniformity.

To produce the novel peanut of the present invention, runner-derived parent lines and varieties possessing the desired agronomic characteristics may be used to advantage, although runner-type germplasm can be used as starting material. In any case, a preferred line can be obtained, following conventional peanut breeding by self-pollination for a number of generations, to usually three or more, of runner-type progeny or of crosses of runner-type with other lines or varieties, selected for high oleic content.

After inbreeding has progressed to the point where progeny are true-breeding for oleic acid content, the runner-derived starting material may be introgressed into diverse peanut backgrounds in the same, or different market classes by breeding methods known in the art. Parent lines and varieties meeting the requirements of the present invention, as set out in greater detail elsewhere herein, can be produced by manipulation of existing peanut materials, using other conventional methods, based on successive selection and inbreeding, or newly developed molecular approaches to altering the genetic content of plants. The production of suitable parent lines and varieties in accordance with the present invention entails the elimination of a certain amount of variability, at least to the extent that an appreciable number of progeny derived from self-pollinating at least one of the parents produce seed having a high oleic acid content.

The high oleic acid trait of 'M2-225' can be introgressed into diverse peanut backgrounds in the same, or different market classes. The high oleic acid trait can be introgressed into other varieties in the runner-type market class (*A. hypogaea* subsp. *hypogaea* var. *hypogaea* botanical type Virginia) as well as the Virginia (*A. hypogaea* subsp. *hypogaea* var. *hypogaea* botanical type Virginia), Peruvian (*A. hypogaea* subsp. *hypogaea* var. *hypogaea* botanical type Peruvian runner), Valencia (*A. hypogaea* subsp. *fastigata* var. *fastigata* botanical type Valencia) and Spanish (*A. hypogaea* subsp. *fastigata* var. *vulgaris* botanical type Spanish) market classes. Peanuts in the runner-type market class are the most commonly used varieties and are found in diverse products such as peanut butter, salted nuts and confectionery products. On the other hand, peanut varieties in the Virginia market class are largely used as salted nuts and in-shell market. The Valencia is largely used in peanut butter while the Spanish type is used in certain niche markets where small round peanuts are needed such as confectionery products and red skin peanuts. Finally, the Peruvian runner market class is grown in certain regions of Mexico.

The high oleic acid trait from 'M2-225' is introgressed into different peanut backgrounds by conventional methods well know to the skilled artisan in the field of peanut breeding. More specifically, crosses are made according to methods described by Norden, A. J., *Peanuts, Culture and Uses,* supra.. Am. Peanut Res. and Educ. Soc., Stillwater, Okla. (C. T.Wilson ed. 1973); Norden, A. J. in *Hybridization of Crop Plants* (H. H. Hadley ed. 1980); Norden, A. J., et al., Breeding of the cultivated peanut in *Peanut Science and Technology,* (H. E. Pattee ed. 1992); Norden, A. J. et al. *Florida Agr. Res.* 3:16–18 (1984), the entirety of each is incorporated by reference. Introgression of the high oleic characteristic has been proceeding using the traditional plant breeding cross pollination techniques. Crosses have been made between 'M2-225' and the following common peanut varieties: AT 108, GK-7, VC-1, Florunner, and AT 120.

The gene or genes responsible for the specific high oleic acid trait in 'M2-225' can be identified using transposon mutagenesis. Methodologies for transposon mutagenesis are known in the art. The following references are incorporated by reference, in their entirety: Walbot, V., *Annual Rev. Plant Phys. & Plant Mol. Biol.* 43:49–82 (1992) Strategies for mutagenesis and gene cloning using transposon tagging and T-DNA insertional mutagenesis; Koncz, N. K. et al., *Plant Mol. Biol.* 20(5):963–76 (1992) T-DNA insertional mutagenesis in Arabidopsis—T-DNA tagging, gene tagging and high-frequency transformation, a review; Baker et al., *PNAS* 83: 4844–4848 (1986); Yoder et al., *Mol. Gen. Genet.* 213: 291–296 (1988); Federoff, N. V., Maize transposable elements. In: Mobile DNA, Berg, D. E. and Howe, M. M. (Eds.) American Society for Microbiology, Washington, D.C. (1989); Belzile et al., *Genetics* 123: 181–189 (1989); Lassner et al., *Mol. Gen. Genet.* 218: 181–189 (1989).

A peanut line is transformed using a transposon known to insert itself into the peanut genome. The presumptive mutants are screened for loss of the high oleic acid trait. Molecular methods are used to analyze and identify the particular locus of the insertional event. Such molecular methods include restriction enzyme digestion and Southern blot analysis using a labelled DNA fragment from the transposon as the hybridization probe to identify the particular DNA fragment containing the "knock-out" insertion. Once a DNA fragment associated with the trait is identified by transposon mutagenesis, the wild-type sequence is cloned from a cDNA or genomic library by methods well known to the skilled artisan. See Gruber, M. Y., et al. in *Methods in Plant Molecular Biology and Biotechnology* (B. R. Glick 1993).

4. Fatty Acid Determinations

Fatty acid distributions are determined by a standard procedure designated "CE 1-62" in OFFICIAL AND TENTATIVE METHODS, Volume 2 (1980), American Oil Chemists Society (AOCS). Alternatively, fatty acid analysis is performed on an HP 5390 gas chromatograph.

The oil derived from the peanut seed of the present invention is of unique character, particularly with regard to the concentration of oleic and linoleic acid. A composite sample of seed from a number of plants may be processed according to methods well known in the art. For example, McWatters, K. H. et al., Potential Food Uses of Peanut Seed Proteins. ch. 18, 689–736 in *Peanut Science and Technology* (H. E. Pattee, ed. 1982) and Fick, G. N. in U.S. Pat. No. 4,627,192, the entirety of each of which is hereby incorporated by reference.

5. Genetic Engineering of Peanuts to Produce High Oleic Acid Varieties

One means to obtain peanut oil with a higher percentage of unsaturated fatty acids is through the genetic engineering of plants, such as that described in the U.S. Pat. No. 5,510,255 to Knauf, et al. 1996. Methods for transformation and regeneration of peanut cells are known. Ozias, P. et al., *Plant Science* 93:185–194 (1993); Norden, A. J., et al., chapter 4, supra. In addition, specific genes associated with improved peanut traits may be introduced using peanut transformation methods known in the art. Ozias-Akins, P. et al., *Plant Science* 93:185–194 (1993).

To genetically engineer a plant a means to transfer genetic material to the plant in a stable and heritable manner is required along with the nucleic acid sequences capable of producing the desired phenotypic result. To produce the desired high oleic acid/low linoleic acid phenotype, requires the Fatty Acid Synthetase (FAS) pathway of the peanut plant is modified to the extent that the ratios of reactants are modulated or changed.

Higher plants appear to synthesize fatty acids via a common metabolic pathway. In developing seeds, where fatty acids attached to triglycerides are stored as a source of energy for further germination, the FAS pathway is located in the proplastids. The first step is the formation of acetyl-ACP (acyl carrier protein) from acetyl-CoA and ACP catalyzed by the enzyme, acetyl-CoA:ACP transacylase (ATA). Elongation of acetyl-ACP to 16- and 18-carbon fatty acids involves the cyclical action of the following sequence of reactions: condensation with a two-carbon unit from malonyl-ACP to form a beta-ketoacyl-ACP (beta-ketoayl-ACP synthase), reduction of the keto-function to an alcohol (beta-ketoacyl-ACP reductase), dehydration to form an enoyl-ACP (beta-hydroxyacyl-ACP dehydrase), and finally reduction of the enoyl-ACP to form the elongated saturated acyl-ACP (enoyl-ACP reductase), beta -ketoacyl-ACP synthase I, catalyzes elongation up to palmitoyl-ACP (C16:0), whereas beta-ketoacyl-ACP synthase II catalyzes the final elongation to stearoyl-ACP (C18:0).

Common plant unsaturated fatty acids, such as oleic, linoleic and alpha-linolenic acids found in storage triglycerides, originate from the desaturation of stearoyl-ACP to form oleoyl-ACP (C18:1) in a reaction catalyzed by a soluble plastid DELTA-9 desaturase (also often referred to as "stearoyl-ACP desaturase"). Molecular oxygen is required for desaturation in which reduced ferredoxin serves as an electron co-donor. Additional desaturation is effected sequentially by the actions of membrane bound DELTA-12 desaturase and DELTA -15 desaturase. These "desaturases" thus create mono- or polyunsaturated fatty acids respectively.

Obtaining nucleic acid sequences capable of producing a phenotypic result in FAS, desaturation and/or incorporation of fatty acids into a glycerol backbone to produce an oil is subject to various obstacles including but not limited to the identification of metabolic factors of interest, choice and characterization of a protein source with useful kinetic properties, purification of the protein of interest to a level which will allow for its amino acid sequencing, utilizing amino acid sequence data to obtain a nucleic acid sequence capable of use as a probe to retrieve the desired DNA sequence, and the preparation of constructs, transformation and analysis of the resulting plants.

Thus, the identification of enzyme targets and useful plant sources for nucleic acid sequences of such enzyme targets capable of modifying fatty acid compositions are needed. Ideally an enzyme target will be amenable to one or more applications alone or in combination with other nucleic acid sequences, relating to increased oleic acid and/or decreased linoleic acid production. Once enzyme target(s) are identified and qualified, quantities of protein and purification protocols are needed for sequencing. Ultimately, useful nucleic acid constructs having the necessary elements to provide a phenotypic modification and plants containing such constructs are needed. Battey, et al., "Genetic engineering for plant oils: potential and limitations," *Trends in Biotech* (1989) 7:122–126; Knauf, "The Application of Genetic Engineering to Oilseed Crops", *Trends in Biotech.* (1987) 5:40–47.

Other objects, features and advantages of the present invention will become apparent from the following detailed description. It should be understood, however, that the detailed description and the specific examples, while indicating preferred embodiments of the invention, are given by way of illustration only. Indeed, various changes and modifications within the spirit and scope of the invention will become apparent to those skilled in the art from this detailed description.

EXAMPLE 1

Origin and Breeding

A high oleic acid peanut variety is developed by chemical mutagenesis of a peanut runner-type variety. Currently available runner-type peanut varieties include 'Florunner', 'Sunrunner', 'GK-7', 'Southern Runner', 'Sunbelt Runner', 'Okrun' and 'AT-108'. Branch, W. D. et al., supra.; 'GK-7', supra.

One parental variety, 'AT-108', was developed from an intervarietal cross between 'GK-7' and 'GK-3'. 'GK-3' is described in Plant Variety Protection certificate 73000094 and 'GK-7' is described in Plant Variety Protection certificate 82001413. 'GK-3' is a very productive Virginia market-type peanut with spreading habit of plant growth and dense foliage. 'GK-7' is a commercial runner-type variety with good productivity and some tolerance to tomato spotted wilt virus. 'GK-7' and 'GK-3' are cross pollinated. F1 seed is planted in the spring and single plant selections are made and planted in the subsequent generations. Selection criteria include runner-type seed and pod size, uniformity, and yield potential.

After continuous selection over several generations, the line is stabilized as a uniform productive commercial runner-type peanut line. Multi-location yield trials are conducted over several years, to determine if the resulting line has a yield advantage over other available runner-type peanut varieties.

Mutagenesis

Seed of a runner-type peanut variety is treated with diethylsulfate (DES) or other known seed mutagen. The seeds are shaken for 15 minutes in a suspension of DES or other mutagen. The seed is rinsed until no odor of the mutagen can be detected. The mutagen-treated seed is placed in a germination chamber to determine the percentage of seed that germinate. The concentration of mutagen used is determined by that amount that permits approximately 30–60% of the seed to germinate. A 1.5% suspension of DES (i.e., 30 ml of DES in 2 liters of water) permitted approximately 50% of the seed to germinate. The sprouted seeds are moved to the field and planted in rows in late Spring/early Summer. In late summer/early fall, individual plants are harvested.

The seed of each individual plant is kept separate for analysis. Three seeds from each plant are analyzed to determine the fatty acid composition of their oil. The tip of the seed is removed before the oil is extracted for analysis. Oil is extracted by solvent extraction. Metcalfe, L. D., et al., *Analytical Chemistry* 33(3):363–364 (1961). The fatty acid analysis is performed on an HP 5390 gas chromatograph. The remaining embryo ends of the seeds are saved for planting.

Sampled seed containing 80% oleic acid, as a percentage of the total fatty acid composition in its oil, are pursued further as expressing the high oleic acid trait. Additional seed samples from plants producing seed with the high oleic acid trait also have their fatty acid profiles analyzed. The remaining seeds are planted in the field in the spring. The seeds harvested in the fall are then analyzed for fatty acid composition and all high oleic seeds are saved for a winter seed increase. Seed harvested in the spring are then analyzed to determine if they are true breeding for the high oleate character.

Phenotype

The variety is analyzed for its phenotype, as compared to other runner-type varieties. The traits analyzed include: color, direction of its mainstem, height, pod size, pod shape, seed size, seed shape, yield, pod splitting, fruiting habit, leaflet size and fatty acid profile. The fatty acid composition of oil from the stabilized variety is compared to other runner-type varieties. The distribution of the following fatty acids is determined: oleic acid, linoleic acid, palmitic acid, stearic acid, arachidic acid, eicosoenic acid, behenic acid, and lignoceric acid. Also, the variation in oleic acid and linoleic acid found in the oil from the stabilized variety is determined.

EXAMPLE 2

Origin and Breeding of 'M2-225'

Definitions

The term "oleic acid content" means the quantity of oleic acid compared to the total fatty acid content of the seed. The term "linoleic acid content" means the quantity of linoleic acid compared to the total fatty acid content of the seed. The term "total fatty acid content of the seed" means that amount of fatty acid extracted from a seed by the method of Metcalf et al., supra. The term "ratio of the amount of oleic acid to linoleic acid in the seed" means a comparison of the oleic acid content to the linoleic acid content. The term "peanut plant having the characteristics of a line designated 'M2-225'" means a peanut plant that produces a runner-type market-type peanut in which the peanut seeds have a high oleic acid content of at least 80%, negligible to no preharvest pod splitting and acceptable or high yield.

The term "peanut plant of the runner-type genetic background" means a peanut plant that was derived from runner market-type parental lines (i.e., varieties in the runner-type market class (*A. hypogaea* subsp. *hypogaea* var. *hypogaea* botanical type Virginia). Examples of runner market-type parental lines include 'AT-108', 'Florunner', 'Sunrunner', 'GK-7', 'Southern Runner', 'Sunbelt Runner' and 'Okrun'. The term "low or negligible pod splitting" means no pod-splitting or less than 1.0% of the total plot weight being comprised of a split pod portion, where the percentage of the total plot weight was calculated for the split pod portion on a weight basis.

The peanut variety, 'M2-225' was developed by chemical mutagenesis of the runner-type variety 'AT-108'. The parental variety, 'AT-108', was developed from an intervarietal cross between 'GK-7' and 'GK-3'. 'GK-3' is a very productive Virginia market-type peanut with spreading habit of plant growth and dense foliage. 'GK-7' is a commercial runner-type variety with good productivity and some tolerance to tomato spotted wilt virus.

Cross pollination of 'GK-3' and 'GK-7' yielded F1 seed. F1 seed was planted in the spring and single plant selections were made and planted in the subsequent generations. Selection criteria were runner-type seed and pod size, uniformity, and yield potential. After continuous selection over nine generations, the line was stabilized as a uniform productive commercial runner-type peanut line. Over five years of multi-location yield trials, the results indicate a yield advantage over currently available runner-type peanut varieties.

Mutagenesis

Seed of 'AT-108' was treated in the spring with diethylsulfate (DES). The seeds were shaken for 15 minutes in a suspension of 30 ml of DES in 2 liters of water. The seed was then rinsed until no odor of DES could be detected. This seed was placed in a germination chamber and approximately 50% of the seed germinated. The sprouted seeds were moved to the field and planted in rows in June. In September, approximately 1700 individual plants were harvested. The seed of each individual plant was kept separate for analysis. Three seed from each plant were analyzed for fatty acid composition of the oil. This was done by removing the tip of the seed and extracting the oil for analysis. The fatty acid analysis was performed on an HP 5390 gas chromatograph. The remaining embryo ends of the seeds were saved for planting.

Three seeds from the plant number 225 were analyzed. It was found that one of the three seeds sampled contained 80% oleic acid as a portion of the total fatty acid composition of its oil. Additional seed samples from plant number 225 contained only wild type fatty acid profiles. The remaining seeds were planted in the field in the Spring. The seeds harvested in the fall were analyzed for fatty acid composition and all high oleic seeds were saved for winter seed increase. Seed harvested in the spring was analyzed and found to be true breeding for the high oleate character.

The peanut variety, 'M2-225' is phenotypically most similar to 'AT-108'. 'M2-225' is a commercial runner-type market-type peanut. Variety 'M2-225' has an alternate fruiting habit as with other Virginia botanical types. It is dark green in color and similar to 'GK-7' and 'AT-108'. It has an erect mainstem but not as tall as 'GK-7'. The mainstem but averages about 22.1 cm in height as compared to 39.6 for 'GK-7'. Pods and seeds are similar in size and shape to 'AT-108'. There is no fruiting on the mainstem and fruiting occurs at alternate nodes. The leaflet averages 2.23 cm in width and 4.83 cm in length. This is smaller than 'GK-7' which has leaflet width of 2.7 cm by 6.65 cm in length.

In three generations of observations, there has been low or negligible pod splitting. Seed and pod size is uniform and similar to 'AT-108'. Yield appears to be similar to 'AT-108', which is an average of 5 to 8% greater than 'GK-7'. The most distinctive characteristic of 'M2-225' is its fatty acid profile, particularly the high oleic acid level, which is 82% in the oil. The 'M2-225' variety also has a acceptable or high yield and no pod splitting.

Table 1 compares the fatty acid composition of oil from 'M2-225' and its parental line 'AT-108'. As a percentage of total fatty acids, 'M2-225' exhibits the following distribution of fatty acids: 81.65% oleic acid, 2.45% linoleic acid, 5.6% palmitic acid, 2.39% stearic acid, 1.66% arachidic acid, 2.09% eicosoenic acid, 2.54% behenic acid, and 2.25% lignoceric acid. By contrast, the parental variety 'AT-108' exhibits the following distribution of fatty acids: 52.78% oleic acid, 25.32% linoleic acid, 9.80% palmitic acid, 3.25% stearic acid, 2.05% arachidic acid, 1.92% eicosoenic acid, 2.75% behenic acid, and 2.25% lignoceric acid.

TABLE 1

A Comparison of Fatty Acid Composition of Oil From 'M2-255' and its Parental Variety

| | % Fatty Acids | | | | | | | |
|---|---|---|---|---|---|---|---|---|
| Variety | Palmitic | Stearic | Oleic | Linoleic | Arachidic | Eicosoenic | Behenic | Lignoceric |
| 'M2-225' | 5.4 | 2.36 | 81.65 | 2.05 | 1.66 | 2.09 | 2.54 | 2.25 |
| AT-108 | 9.80 | 3.25 | 52.78 | 25.32 | 2.05 | 1.92 | 2.75 | 2.13 |

Table 2 compares the variation in oleic acid and linoleic acid found in the oil from 'M2-225' and its parental line 'AT-108'. As a percentage of total fatty acids, 'M2-225' exhibits from about 77.25% to 86.23% oleic acid as compared to the range of variation found in 'AT-108' from about 48.25% to about 54.53% oleic acid. 'M2-225' exhibits a lower concentration of linoleic acid from about 1.75% to 3.1% as compared to the range of linoleic acid concentration found in 'AT-108' from about 32.22% to 22.34%.

TABLE 2

A Comparison of the Variation in Oleic Acid and Linoleic Acid Composition of 'M2-225' and 'AT-108'

| Varieties | Oleic Acid | Linoleic Acid |
|---|---|---|
| 'M2-225' | 77.25 to 86.23% | 1.75 to 3.1% |
| 'AT-108' | 48.25 to 54.53% | 32.3 |

The pod splitting characteristics of the 'M2-225' variety was compared to the "SunOleic® 95R" variety. Yield trials for the 'M2-225', AT 108 and "SunOleic® 95R" varieties at three locations provided the source of samples for pod splitting evaluation. The trials were arranged in a Randomized Complete Block design with four replications. Each plot size had 2 rows that were each 20 feet long. A 500 gram sample was taken from each plot and all split pods were removed and weighed. A percentage of the total plot weight was calculated for the split pod portion. When the number of split pods was less than two, the sample results were recorded as <0.10%. The data is presented in Tables 3 and 4. 'M2-225' has less than 0.1–0.3% pod splitting, while SunOleic® 95R has 1.0–7.0% pod splitting. The 'M2-225' variety has a significant and advantageous trait due to its significantly lower pod splitting characteristic. The frequency of pod-splitting found in 'M2-225' is compared to that found in 'AT-108' and 'SunOleic® 95R' in Tables 3 and 4.

The Randomized Complete Block design with four replications at each of three locations provided the yield data for the 'M2-225', AT 108 and "SunOleic® 95R" varieties. The yields for each of these varieties was recorded in pounds of unhulled peanuts per acre, as presented in Table 5. The 'M2-225' variety is significantly higher yielding than the "SunOleic® 95R" variety. 'M2-225' does not have a significantly different yield from the source variety, AT108.

TABLE 3

A Comparison of the Objective Characteristics of 'M2-225' to Other Runner-type Peanut Seeds and Plants

| Variety | % Oil | % Protein | Oleic/ linoleic ratio | Iodine number | Shelling % | 5 mk % | EIK % | Main stem height | % Pod splitting |
|---|---|---|---|---|---|---|---|---|---|
| 'M2-225' | 52.0 | 26 | 50 | 74 | 78 | 76 | — | 21 | <0.10% |
| 'AT 108' | 52. | 26 | 1.9 | 94 | 78 | 76 | — | 21 | <0.10% |
| 'Sun Oleic 95 R' | 47.0 | 29 | 23 | 77 | 78 | 74 | — | 49 | 1.00–7.00% |

TABLE 4

A comparison of the pod splitting characteristic of 'M2-225' and 'SunOleic ® 95R'

| | | % Pod Splitting | |
|---|---|---|---|
| Location | Replication | 'M2-225' | SunOleic |
| Ashburn, GA | 1 | <0.10% | 3.00% |
| | 2 | <0.10% | 4.00% |
| | 3 | <0.10% | 5.00% |
| | 4 | <0.10% | 7.00% |
| Statesboro, GA | 1 | <0.10% | 1.00% |
| | 2 | <0.10% | 2.00% |
| | 3 | <0.10% | 3.00% |
| | 4 | <0.10% | 5.00% |
| Pleasanton, TX | 1 | <0.10% | 6.00% |
| | 2 | <0.10% | 2.00% |
| | 3 | <0.10% | 3.00% |
| | 4 | <0.10% | 4.00% |

TABLE 5

Yield comparision of 'M2-225', 'AT 108' and 'Sunoleic ® 95R' (pounds of unhulled peanuts per acre)

| Location | 'M2-225' | 'AT 1-8' | 'SunOleic ® 95R' |
|---|---|---|---|
| Ashburn, GA | 3539 | 3655 | 3230 |
| Statesboro, GA | 3856 | 3745 | 3059 |
| Pleasanton, TX | 4590 | 4325 | 4120 |

Milling characteristics were evaluated on 'M2-225', AT 108, and 'SunOleic® 95R' to determine the percentage of total seed that comprised of: (1) Sound Mature Kernels (SMK); (2) Sound Splits (SS); (3) Total Sound Mature Kernels (TSMK) and (4) Other Kernels (OK). This milling characteristics are shown in Table 6. Blanchability was determined by running a 500 g sample through a pilot plant blancher and the percentage of kernels retaining seed coat was calculated. Grades and kernel sizing were determined by the standard USDA peanut grading and sizing procedure. The blanchability and grades are shown in Table 7.

TABLE 6

Milling Characteristics

| | % Hulls | % SMK | % SS | % TSMK | % OK | % Damage | % No. 1's | % Medium Runners | % Jumbo Runners |
|---|---|---|---|---|---|---|---|---|---|
| Entry | 23.0 | 71.0 | 3.0 | 74.0 | 3.0 | 4.0 | 8.0 | 34.0 | 28.0 |
| 'M2-225' | 26.0 | 70.0 | 2.0 | 72.0 | 5.0 | 3.0 | 8.0 | 33.0 | 25.0 |
| 'Sunoleic ® 95R' | 24.0 | 69.0 | 1.0 | 70.0 | 5.0 | 3.0 | 10.0 | 34.0 | 25.0 |

TABLE 7

| | Blanchability |
|---|---|
| Entry | % Unblanched Kernels |
| 'M2-225' | 0% |
| SunOleic ® 95R | 0.10% |
| AT 108 | 0% |

EXAMPLE 3

Mode of Inheritance and Breeding of New High Oleic Peanut Varieties

Cross pollinations were made between the mutant 'M2-225' line and the parental variety AT 108. Both reciprocal crosses were made. The F2 seed from that cross was recovered and fatty acid analysis was performed using an HP 5890 gas chromatograph. The results are summarized in Table 8. The X2 values indicate the segregating ratios to be 3:1. The data therefore show that the 'M2-225' high oleic characteristic fits a simple Mendelian model of a single recessive gene that must be homozygous for expression.

In view of the genetics of the high oleic trait characterized in variety 'M2-225', new high oleic varieties of peanut can be easily made. The high oleic trait from 'M2-225,' which is controlled by a single recessive gene, can be predictably and reproducibly introgressed into diverse genetic backgrounds of peanut using methods well know to the skilled artisan. For example, 'M2-225' is crossed as the male or female parent to another peanut line with desired agronomic characteristics. Progeny are selected and selfed to produce lines that are homozygous recessive for the high oleic trait combined with other desired traits. Alternatively, the progeny are backcrossed to one of the parents over one or more generations prior to the step of selfing. The skilled artisan can envision many other breeding strategies in which the high oleic trait is combined with other agronomic characteristics to produce new peanut cultures.

TABLE 8

| Parents | | Low Oleic | High Oleic | Low Oleic | High Oleic | | |
|---------|---|-----------|------------|-----------|------------|---|---|
| Female | Male | Observed | Observed | Expected | Total Expected | | X2 |
| AT 108 | 'M2-225' | | | | | | |
| | 1 | 40 | 10 | 37.5 | 12.6 | 50 | 0.4142162 |
| | 2 | 4 | 3 | 5.25 | 1.75 | 7 | 0.2752338 |
| | 3 | 23 | 9 | 24 | 8 | 32 | 0.6830914 |
| 'M2-225' | AT 108 | | | | | | |
| | 1 | 27 | 13 | 30 | 10 | 40 | 0.2733219 |
| | 2 | 89 | 25 | 85.5 | 28.5 | 114 | 0.4490299 |
| | 3 | 19 | 6 | 16.5 | 5.5 | 22 | 0.5148277 |

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A peanut seed having an oleic acid content of from about 80% to about 85% and a linoleic acid content of from about 1.5% to about 2.5%, each based upon the total fatty acid content of said seed and a ratio of the amount of oleic acid to linoleic acid in said seed from about 7:1 to about 80:1, wherein said seed has the characteristic of low pod splitting that is less than 1% and said seed is the product of either (1) a peanut plant line designated 'M2-225' having American Type Culture Collection (ATCC) deposit accession No. 97762 or (2) a peanut plant line having a pedigree that includes 'M2-225'.

2. A peanut seed that is the product of a peanut plant line designated 'M2-225' having ATCC deposit accession No. 97762.

3. A peanut seed according to claim 1, wherein said seed is the product of a peanut plant of the runner-type genetic background.

4. A peanut seed according to claim 1, wherein said seed is the product of a peanut plant having the characteristic of an acceptable milling characteristic of a grade of at least about 75.

5. A peanut plant which produces seeds having an oleic acid content from about 80% to about 85% and a linoleic acid content of from about 1.5% to about 2.5%, each based upon a total fatty acid content of said seed and a ratio of the amount of oleic acid to linoleic acid in said seed from about 7:1 to about 80:1, wherein said seeds have the characteristic of low pod splitting that is less than 1%, and wherein said plant is the product of either (1) seed of a peanut plant line designated 'M2-225' having ATCC deposit accession No. 97762 or (2) seed of a peanut plant line having a pedigree that includes 'M2-225'.

6. A peanut plant designated 'M2-225' which is produced from seeds having ATCC deposit accession No. 97762.

7. A peanut plant according to claim 5, wherein said peanut plant is of the runner-type genetic background.

8. A peanut plant according to claim 5, wherein said peanut plant has the characteristic of an acceptable milling characteristic of a grade of at least about 75.

9. An Arachis hypogaea L. seed product consisting essentially of a substantially homogenous assemblage of peanut seeds having an oleic acid content of from about 80% to about 85% and a linoleic acid content of from about 1.5% to about 2.5%, each based upon the total fatty acid content of said seed and a ratio of the amount of oleic acid to linoleic acid in said seed from about 7:1 to about 80:1, wherein said seed has the characteristic of low pod splitting that is less than 1%, wherein the seed of said seed product is the product of either (1) a peanut plant line designated 'M2-225' having ATCC deposit accession No. 97762 or (2) a peanut plant line having a pedigree that includes 'M2-225'.

10. A seed product of a peanut plant line designated 'M2-225' having ATTC deposit accession No. 97762.

11. A seed product according to claim 9, wherein said seed is the product of a peanut plant that is of the runner-type genetic background.

12. A seed product according to claim 9, wherein said peanut seed is the product of a peanut plant that has the characteristic of an acceptable milling characteristic of a grade of at least about 75.

13. A peanut line consisting essentially of a substantially uniform population of Arachis hypogaea L. plants which produce seed having an oleic acid content of from about 80% to about 85% and a linoleic acid content of from about 1.5% to about 2.5%, each based upon the total fatty acid content of said seed and a ratio of the amount of oleic acid to linoleic acid in said seed from about 7:1 to about 80:1, wherein said seed has the characteristic of low pod splitting that is less than 1%, and wherein said peanut line is either (1) a peanut plant line designated 'M2-225' having ATCC deposit accession No. 97762 or (2) a peanut plant line having a pedigree that includes 'M2-225'.

14. A peanut line designated 'M2-225' having ATCC deposit accession No. 97762.

15. A peanut line according to claim 13, wherein said plants are of the runner-type genetic background.

16. A peanut line according to claim 13, wherein said plants having the characteristic of an acceptable milling characteristic of a grade of at least about 75.

17. A peanut seed according to claim 1, wherein said ratio of the amount of oleic acid to linoleic acid in said seed is from about 20:1 to about 58:1.

18. A peanut seed according to claim 1, wherein said seed is the product of a peanut plant having acceptable blanching.

19. A peanut plant according to claim 5, wherein said plant produces seed having acceptable blanching.

20. A seed product according to claim 9, wherein said product is the product of a peanut plant having acceptable blanching.

21. A peanut line according to claim 13, wherein said plant has acceptable blanching.

22. A peanut line according to claim 13, wherein said plants have acceptable yield.

23. A peanut line according to claim 13, wherein said plants have a high yield.

24. Plant parts of the peanut line designated 'M2-225' having ATCC deposit accession No. 97762.

25. The plant parts of claim 24, wherein said parts are selected from the group consisting of pollen, seeds and pods.

* * * * *